United States Patent [19]

Takano et al.

[11] 4,133,857
[45] Jan. 9, 1979

[54] METHOD FOR PRODUCING A GRANULAR SORBIC ACID

[75] Inventors: Masaaki Takano; Masahiro Nakajima, both of Minamatashi, Japan

[73] Assignee: Chisso Corporation, Osaka, Japan

[21] Appl. No.: 692,626

[22] Filed: Jun. 3, 1976

[30] Foreign Application Priority Data

Sep. 16, 1975 [JP] Japan .................................. 50-111892
Oct. 16, 1975 [JP] Japan .................................. 50-124677
Apr. 9, 1976 [JP] Japan .................................. 51-40051

[51] Int. Cl.² .............................................. B01J 2/20
[52] U.S. Cl. ................................... 264/120; 264/109; 264/141; 562/580
[58] Field of Search ..................... 264/109, 141, 120; 260/526 N

[56] References Cited

U.S. PATENT DOCUMENTS

| 2,833,750 | 5/1958 | Vickers | 264/141 |
| 2,841,528 | 7/1958 | Myhre | 264/109 |
| 3,146,493 | 9/1964 | Steinle et al. | 264/141 |
| 3,758,563 | 9/1973 | Vematsu | 260/526 N |
| 3,887,614 | 6/1975 | Susuki et al. | 264/141 |

Primary Examiner—Robert F. White
Assistant Examiner—James R. Hall
Attorney, Agent, or Firm—Fred Philpitt

[57] ABSTRACT

A granular sorbic acid having improved properties is prepared in a very simple manner without need of any particular preparation as in conventional methods, i.e. by granulating by extrusion, powder having particle sizes of ASTM No. 70 sieve pass in the presence of water or water containing a surfactant. The resulting granule has a suitable hardness and hence scarcely collapses at the time of drying after granulation and subsequent handling, but has a rapid dispersibility into foods at the time of its use.

11 Claims, No Drawings

METHOD FOR PRODUCING A GRANULAR SORBIC ACID

DESCRIPTION OF THE INVENTION

The present invention relates to a method for producing a granular sorbic acid. More particularly, it relates to a method for preparing a granular sorbic acid in a simple manner without any tackifier or additive except for water or water and a small amount of a surfactant.

Sorbic acid as well as potassium sorbate have recently been extensively used as an additive to foods. As for the form of sorbic acid to be employed, since sorbic acid is hardly soluble in water, it is used in such a manner that its powder is blended or kneaded with oily or solid foods. Thus, if the powdery product of sorbic acid has paticle sizes which pass through ASTM No. 70 sieve (the terms "particle sizes which pass through ASTM No. 70 sieve" will hereinafter be abbreviated merely as "particle sizes of 70 mesh pass" or "particle sizes of ASTM No. 70 sieve pass"; particle sizes which pass through ASTM Nos. 100, 140, 300 and 400 sieves will also hereinafter be similary abbreviated; also, in the case of particle sizes which do not pass through ASTM No. 70 sieve, the terms "particle sizes which do not pass through ASTM No. 70 sieve" will hereinafter be abbreviated merely as "particle sizes of 70 mesh on" or "particle sizes of ASTM No. 70 sieve on"; and this applies to the cases of other Nos. sieves), especially powder sizes of 100 mesh pass, and particularly if the powdery product contains fine powder having powder sizes of 140 mesh pass, especially 300 mesh pass, then such powder is liable to scatter as powder dust when blended with foods, or even if they do not scatter, uniform dispersion thereof into oily or solid foods at the time of blending is liable to take time. On the other hand, if coarse powder of sorbic acid such as those of 50 mesh on is blended or kneaded with oily or solid foods, the powder is liable to be unevenly distributed, and hence undesirable in the point of uniform dispersion.

On the other hand, as for potassium sorbate, if it is unsuitable for use because of its form of powder or fine powder, those of known granule may be used (note: those containing no additive are known, e.g. Japanese patent publication No. 38131/1971). Further, since potassium sorbate is soluble in water, dispersion or dissolution thereof into foods containing water may be smoothly effected. As in the case of potassium sorbate, granular form of sorbic acid is also known (Japanese patent publication No. 31094/1974), in which potassium sorbate is used as a tackifier for granulation, but, since such granular contains a material other than sorbic acid, its use tends to be limited. Further, a granular sorbic acid in which no tackifier nor additive is used is also known (Japanese patent application laid-open No. 83324/1975), but, in this case, since the powder size, the water content employed, etc. are strictly limited, in other words, since the usable range of powder sizes of raw material is comparatively narrow, the preparation conditions are restricted and the resulting granular product is relatively hard and difficult to collapse, thus the granule has also a drawback in that dispersion thereof into foods is somewhat difficult.

The present inventors have made strenuous studies on a method for producing a granular sorbic acid having almost no drawbacks as mentioned above. As a result, we found at first a method wherein only powder of sorbic acid having specified powder sizes and water are used (method (2) mentioned below).

According to this method, a mixture of less than 80% by weight of powder of sorbic acid having particle sizes of 70 mesh pass with 20% by weight or more of extremely fine powder thereof having particle sizes of 20μ or smaller, or said extremely fine powder alone, is granulated by extrusion in the presence of water to give a granular sorbic acid.

The percentage (%) referred to herein all means percentage by weight.

The above-mentioned method is superior in that no additive other than water is used and fine powder which is difficult to use as it is can be utilized, but, on the other hand, extremely fine powder as small as 20μ or smaller which must be purposely prepared is required.

The present inventors have made a further study on a method for producing a granular sorbic acid which is more rapid in dispersing into foods at the time of its use, and as a result, found that when fine powder of sorbic acid having powder sizes of 70 mesh pass, water and a surfactant are used together, granulation is possible without using extremely fine powder of sorbic acid, and since the resulting product is hard, collapse at the time of drying and handling is less and hence the yield is superior (methods (5), (6) and (7) mentioned below).

As apparent from the foregoing, a first object of the present invention is to provide a method for producing a granular sorbic acid by using a sorbic acid which does not require any particular preparation except that it is of powder or fine powder or extremely fine powder, and without using any tackifier or extender except that water or water together with a small amount of surfactant are used, and also to provide the resulting product thus prepared.

A second object of the present invention is to provide a method for producing a granular sorbic acid having a suitable hardness due to which the tendency of collapse during the drying process after granulation and at the time of handling after preparation is less.

A third object of the present invention is to provide a granular sorbic acid which is rapid in dispersing into foods at the time of its use (i.e. at the time of adding to foods). Other objects will become apparent by way of the description mentioned below.

The present invention resides in the following main method (1) and several embodiments (2)-(9):

(1) A method for producing a granular sorbic acid which comprises granulating by extrusion, powder of sorbic acid having particle sizes of ASTM No. 70 sieve pass in the presence of water or water containing a surfactant;

(2) A method according to the above-mentioned method (1) wherein said powder of sorbic acid having particle sizes of ASTM No. 70 sieve pass consists of a mixture of less than 80% by weight of said powder with 20% by weight or more of fine powder of sorbic acid having particle sizes of 20μ or smaller or said fine powder alone, and said granulation is carried out in the presence of water;

(3) A method according to the above-mentioned methods (1) or (2) wherein said powder of sorbic acid having particle sizes of ASTM No. 70 sieve pass consists of 50 - 75% by weight of powder of sorbic acid having particle sizes of ASTM No. 70 sieve pass to ASTM No. 300 sieve * on and 50 - 25% by weight of fine powder of sorbic acid having particle sizes of 20μ or smaller;

(4) A method according to the above-mentioned methods (2) or (3) wherein the amount of water used is in the range of 10-50% by weight based on the total sum of the amounts of said powder of sorbic acid, said fine powder of sorbic acid and water;

(5) A method according to the above-mentioned method (1) wherein powder of sorbic acid having particle sizes of ASTM No. 100 sieve pass is granulated by extrusion in the presence of water and a surfactant having a HLB (hydrophilelypophile balance) of 7 or more;

(6) A method according to the above-mentioned method (1) wherein powder of sorbic acid having particle sizes of ASTM No. 70 sieve pass is granulated by extrusion in the presence of water and a surfactant having a HLB of less than 7 and containing a polyoxyethylene sorbitan fatty acid ester as an effective ingredient;

(7) A method according to the above-mentioned methods (5) or (6) wherein the amounts of water and said surfactant used are in the ranges of 4-15% by weight and 0.02-1.0% by weight based on the total weight of water and said powder of sorbic acid, respectively;

(8) A method according to the above-mentioned methods (1) - (7) wherein the resulting product obtained by said granulation by extrusion is further granulated by extrusion repeatedly;

(9) A method according to the above-mentioned methods (1) - (8) wherein the resulting product obtained by said granulation by extrusion is dried under the atmospheric pressure or a reduced pressure at a temperature of 80° C. or lower;

(10) A method according to the above-mentioned method 9 wherein said drying is carried out in a fluidized bed; and

(11) A method according to the above-mentioned method 9 wherein said drying is carried out in an aeration manner. *ASTM No. 300 sieve: The list of sieves based upon ASTM standard specifies No. 270 and No. 325 sieves but not No. 300. We prepared a sieve corresponding to ASTM No. 300 sieve this time from the data of openings for No. 270 and No. 325 (i.e. a sieve having openings of 46μ).

The constitutions and effectivenesses of the present invention will be described below in detail.

The powder of sorbic acid having particle sizes of 70 mesh pass employed in the method of the present invention (abbreviated as powder of sorbic acid of 70 mesh pass) can be readily obtained by recrystallizing sorbic acid from water or an organic solvent, followed by drying and separating by a sieve, relatively coarse powder having particle sizes of 70 mesh on. If coarse powder of 70 mesh on is contained, for example, those of 50 mesh on are contained in an amount of 10%, granulation becomes very difficult, and even if granulation is effected, the resulting product is liable to collapse at the time of handling. Thus, admixture of coarse powder of 70 mesh on should be avoided.

The main range of particle size distribution of powder of sorbic acid of 70 mesh pass varies depending on the recrystallizing manner of sorbic acid, and may be 70-140 mesh and also may be 100-300 mesh according to preparation manner. Further, powder of sorbic acid containing a large amount of extremely fine powder as small as 300 mesh pass may be also employed without any difficulty, although the main range of particle size distribution of powder of sorbic acid used in the present invention is 70 mesh pass to 300 mesh on. To the contrary, however, if coarse powder of 100 mesh on, particularly 70 mesh on or powder of 70 mesh pass and 100 mesh on is contained in a large amount, granulation becomes difficult, and even if granulation is effected, the resulting granule is liable to collapse at the time of handling, except for the case of the above-mentioned method (6) using a specified surfactant. Accordingly, admixture of a large amount of coarse powder of 70 mesh pass and 100 mesh on should be generally avoided. This, however, does not mean that even if such coarse powder is contained in a very small amount, e.g. a few %, it becomes impossible to conduct the method of the present invention. If such coarse powder is contained in a small amount, a result of the next best is obtained. Further, even if coarse powder of 70 mesh pass and 100 mesh on is contained in a relatively large amount, repeated granulation carried out as described in the above-mentioned method (8) or Examples 19 and 20 mentioned below enables to obtain a granular sorbic acid to a practically feasible extent due to its kneading effect.

The sorbic acid to be employed in the method of the present invention, prepared in advance so as to make the powder of 100 mesh pass and 300 mesh on occupy the greater part of the particle size distribution, is obtained by separating coarse powder by means of ASTM No. 100 sieve. On the other hand, it is unnecessary to separate by sieve, fine powder such as those of 300 mesh pass, but such powder rather brings about a desirable result. Even when very fine powder such as 300 mesh pass occupies the total amount of powder, such powder is usable although there is no such necessity in practice.

Powder of sorbic acid having particle sizes of 20μ or smaller, to be employed in the method of the present invention (which will hereinafter be abbreviated as fine powder of sorbic acid), is prepared according to either of the methods mentioned below:

Crystalline powder of sorbic acid is pulverized according to a mechanical method, or a solution of sorbic acid in hot water or an organic solvent is diluted with a non-solvent such as water or others, preferably rapidly diluted and cooled, to precipitate fine powder of sorbic acid. A particularly desirable method is that described in Japanese patent application No. 66688/1975 or in the former half of Example 1 mentioned below. The resulting sorbic acid thus obtained is extremely fine particle having particle sizes as small as 1μ or smaller, and yet superior in property of being dehydrated by filtration. Such fine particle forms a paste having a water content of about 50% or a slurry or suspension having a water content of 60% or more, and can be used for granulation of the present invention as it is or after reducing water content by drying or filtration.

As for the water to be employed in the method of the present invention, those which are extremely small in vaporization residue or ash such as distilled water or softened water are preferable. The specific feature of the above-mentioned methods (5), (6) and (7) of the present invention consists in the small amount of water required, e.g. such a small amount of 4-15% by weight, preferably 5-10% by weight based on the total sum (100% by weight) of the amounts of water and powder of sorbic acid having particle sizes of 100 mesh pass may be sufficient. On the other hand, according to the above-mentioned methods (2), (3) and (4) of the present invention, such a large amount of water as 10-45% is necessary based on the total sum of the amounts of water and powder of sorbic acid and/or fine powder of sorbic acid. Accordingly, the drying time in the case of these methods (2), (3) and (4) tends to be prolonged as compared with the case of the above-mentioned methods (5), (6) and (7).

As for the surfactant to be employed in the methods (1), (5), (7) and (9), those having a HLB of 7 or more may be preferably employed.

From the viewpoint of granulation effect, the surfactants may have the HLB of 7 or more either in one kind or in a mixture of two or more kinds, and any kinds may be employed for the surfactants. Namely, even if a surfactant has a HLB less than 7, it may be employed if it is mixed with a surfactant having a HLB higher than 7 in a suitable proportion to give a HLB of 7 or more in total. Thus, almost all of the surfactants which satisfy the above-mentioned requirement may be employed. However, an exceptional case is the one where a polyoxyethyene sorbitan fatty acid ester is employed in admixture (the above-mentioned method (6)). In this case, even if the HLB is less than 7, an effective granulation is possible.

On the other hand, considering the fact that sorbic acid is used as an additive to foods, the surfactants must not be poisonous although the amount thereof added is extremely small.

Accordingly, for practical use, almost all of cationic and anionic surfactants should be excluded from the objectives to be selected for the use in the method of the present invention, and also a considerable number of nonionic surfactants should be excluded from the objectives.

For the above-mentioned reason, the surfactants to be employed in the method of the present invention are preferably selected from the following kinds in practical use:

In the first place, sucrose fatty acid esters are mentioned such as monoesters, diesters and triesters of sucrose with one kind of higher fatty acids such as lauric acid, milistic acid, palmitic acid, stearic acid, oleic acid, linolic acid and the like, polyesters of sucrose with 4 or more kinds of higher fatty acids and mixtures of the foregoing esters.

Next sorbitan fatty acid esters are mentioned such as monoesters, diesters, triesters and tetraesters of sorbitan with higher fatty acids as mentioned above and mixtures of these esters.

Further there are mentioned glycerine fatty acid esters such as monoesters, diesters and triesters of glycerine with higher fatty acids as mentioned above and mixtures of these esters, and propylene glycol fatty acid esters such as monoesters and diesters or propylene glycol with higher fatty acids as mentioned above and mixtures of these esters.

Still further there are mentioned polyoxyethylene sorbitan fatty acid esters such as monoesters, diesters, triesters and tetraesters of sorbitan-polyoxyethylene addition compounds with higher fatty acids as mentioned above and mixtures of these esters, and polyglycerine fatty acid esters such as monoesters, diesters, triesters and polyesters of polyglycerine with higher fatty acids as mentioned above and mixtures of these esters.

Furthermore, esters of the above-mentioned polyols and polyol fatty acid esters having free alcohol groups with lactic acid, succinic acid, fumaric acid, malic acid, tartaric acid, and lactic acid fatty acid esters and tartaric acid fatty acid esters having free acid groups can be also employed.

Further, esters of higher fatty acids as mentioned above (lauric acid, milistic acid, palmitic acid, stearic acid, oleic acid, linolic acid and the like) with such organic compounds having hydroxyl groups as lactic acid, potassium lactate, sodium lactate, malic acid, potassium malate, tartaric acid, potassium tartarate, sodium tartarate, citric acid, potassium citrate, sodium citrate and the like, and lecithin, hydroxide of lecithin, etc. can be also employed.

These surfactants can be used in one kind or in a mixture of two or more kinds and they have preferably a HLB of 7 or more in total, as mentioned above. The amount thereof used is 0.02–1.0%, preferably 0.05–1.0% based upon the weight of sorbic acid. Too small an amount makes granulation impossible, while too large an amount does not result in any particular improvement of effectiveness. On the other hand, however, in the case of the above-mentioned method (6) wherein a polyoxyethylene sorbitan fatty acid ester is contained as an effective ingredient in the surfactant to be employed, granulation is possible even if the surfactant has a HLB less than 7.

Further, a small amount of other additives than the above-mentioned water and surfactants may be mixed with the granular sorbic acid which is the objective of the method of the present invention, in order to maintain and improve the quality and properties of the granular sorbic acid product. For necessary heat stability to be maintained (antioxidation), e.g. erysorbic acid, BHT, BHA, gallic acid and esters thereof, phytic acid and salts thereof, etc. are mentioned. For improving the dispersibility and collapsibility of the granular sorbic acid in foods at the time of its use, polyphosphates such as sodium tripolyphosphate are mentioned.

Powder of sorbic acid having particle sizes of 70 mesh pass, water, surfactant and other additive to be employed in the method of the present invention can be mixed in any known manner. Namely, said powder of sorbic acid may be wetted with water and then a surfactant is mixed with the resulting material, or said powder may be wetted with a solution of said surfactant.

For mixing, various known mixers or blenders such as Henschel mixer, ribbon blender, V type blender, rotating drum type mixer, etc. may be employed. The mixing may be carried out at a temperature of 50° C. or lower, preferably room temperature or lower, for example for one hour or shorter, preferably for 10–30 minutes, preferably in an inert gas atmosphere such as that of nitrogen gas.

As for the granulator for the mixture of powder of sorbic acid and water and if necessary, a surfactant, to be employed in the method of the present invention, any known granulator may be employed in principle. For example, those of rotating drum type, plunger type, tabletting type, extrusion type, etc. are mentioned, and among them, an extrusion type granulator is preferable because granules having a uniform size can be prepared with a reliability.

The above-mentioned words "in principle" were used on account of the following reason:

Since the granule of sorbic acid which is expected to be used practically, has a volume as a unit granule, of 0.1 ml or smaller, particularly in the range of about 0.05 – 0.0001 ml, a granulator for preparing such large granule as those exceeding 0.1 ml is not practical. Because the demand of granule for such large particles is not expected in the market at present or in the near future.

The above-mentioned granulators may be operated in a known manner.

Extruded granule, i.e. undried granule is dried up to a water content of 0.5% or less, preferably about 0.1%–0.3%, by means of aeration with hot air or using a known dryer such as a fluidized dryer, a vacuum dryer or the like. The temperature of hot air to be employed is 80° C. or lower, preferably 70° C. or lower, and the temperature inside the dryer is maintained at 70° C. or lower, preferably 60° C. or lower. At temperatures exceeding these, the resulting granular product is apparently or latently degraded, or there is a fear of degradation. The period of time necessary for drying varies depending upon the kind of undried granule (powder size distribution), the composition (the contents of water and surfactant) and further the conditions of dryer, and drying is completed at the longest within two hours, usually within one hour. After completion of drying, the granule is cooled down to 40° C. or lower, preferably room temperature, by being allowed to stand or aeration or cooling through the wall of dryer. The resulting granule is taken out and powdered substance is separated by sieve to give a product of granular sorbic acid.

Further, in the case of the above-mentioned repeated granulation as described in the method (8) or Examples 19 and 20 mentioned below, which is necessary when powder of sorbic acid having particle sizes of 70 mesh pass to be employed contains coarse powder of 70 mesh pass and 100 mesh on in a comparatively large amount such as 10% or more, it is possible to employ undried granule together with a section of powder of sorbic acid of 70 mesh pass whose granulation was not effected. Subsequent drying is carried out in the same manner as mentioned above.

Granular product of sorbic acid obtained according to the above-mentioned methods (5) or (7) of the present invention is harder than that obtained according to the above-mentioned methods (2) or (4) of the present invention, and is not readily broken into powder by pressing. Accordingly the dried product is scarcely powdered during handling. On the other hand, when it is introduced into water, dispersion is rapidly and readily effected, and thus, when it is kneaded into foods, dispersibility is very good.

According to the method of the present invention, granulation is effected only by mixing together powder of sorbic acid having particle sizes of 70 mesh pass, fine powder of sorbic acid having particle sizes of 20 $\mu$ or smaller and water or water and a small amount of a surfactant having a HLB of preferably 7 or more, and no organic solvent is employed. Thus, recovery of solvent is unnecessary. Further since any tackifier or other additives are not employed beside water or water and a specified small amount of a surfactant, no disagreeable taste nor smell is imparted to the foods in which the granular product of the present invention is employed. Furthermore, it is unnecessary to employ any particular apparatus. Still further, as for the powder of sorbic acid to be employed in the method of the present invention, those having particle sizes of 70 mesh pass are sufficient, and no particular particle size distribution is required. Further, as for the method for preparing fine powder of sorbic acid having particle sizes of 20 $\mu$ or smaller, to be employed in the method of the present invention, no particularity is required.

The method of the present invention will hereinafter be illustrated by way of the following Referential example, non-limitative Examples and Comparative examples.

Referential example

Powder of sorbic acid on sale (made by Chisso Corporation) was separated by sieve, and granulation was attempted using water alone, with each of the resulting separated powders having various ranges of particle sizes.

The ranges of particle sizes of samples are as follows:

| Sample No. | Range of particle sizes | Note |
| --- | --- | --- |
| Product on sale | 40 mesh totally pass | Fine powder of 20 $\mu$ or smaller is not contained. |
| 1. | 60 mesh on | |
| 2. | 60 mesh pass, 70 mesh on | |
| 3. | 70 mesh pass, 100 mesh on | |
| 4. | 100 mesh pass, 140 mesh on | |
| 5. | 140 mesh pass, 300 mesh on | |
| 6. | 300 mesh pass | |

With each of the above-mentioned samples 1–5, a sufficient amount of water is mixed to give a plasticized state, followed by granulation by means of an extrusion type granulator (hole diameter: 1 mm). If granulation was effected, the resulting granule was subjected to aeration drying (at 60° C. for one hour). The product on sale and samples 1 and 2 could not be granulated. Samples 3, 4 and 5 could be granulated, but, after drying, the resulting granule collapsed into the original powder. As a result, no granular product was obtained.

EXAMPLE 1

1000 Parts of a hot aqueous solution of sorbic acid (99° C., concentration: about 3%) were spouted at this temperature into a vacuum system maintained under a reduced pressure of 30–40 mmHg, and cooled, to give a suspension in which the most part of sorbic acid precipitated. This suspension was subjected to decantation, followed by filtration to give 35 parts of a paste-like sorbic acid having a water content of 51%. The particle sizes thereof were measured by observation through a microscope. As a result, the particle sizes of the most part of the particles were 1 $\mu$ or smaller. Ten parts of the above-mentioned paste-like substance were thinly spread on a glass plate and dried at room temperature under a reduced pressure of 20 mmHg up to a water content of 35%. Seven parts of the resulting substance were granulated by means of an extrusion type granulator having a hole diameter of 1 mm, followed by drying at 60° C. for one hour in a nitrogen gas current to give 4.6 parts of a granular product. In addition, a relationship between the water content and the capability of being granulated, of the paste-like substance was studied. As a result, the preferable range of water content was found to be 15–45%.

EXAMPLE 2

A crystalline sorbic acid prepared according to a conventional method was dissolved in methanol at 58° C. to give a saturated solution, which was then poured into 10 times amount of cooled water under rapid stirring to crystallize out fine powder of sorbic acid. The resulting liquid, while being maintained at room temperature, was subjected to vacuum distillation under rapid stirring to remove methanol. The resulting suspension of sorbic acid was, as it was, passed through ASTM No. 400 sieve to remove particles having comparatively large particle sizes, followed by decantation and filtration to give a filtered substance of sorbic acid having a water content of 26%, which was then granulated by means of an extrusion type granulator. Granule was easily obtained. After drying, the resulting granule has superior properties.

Further, the particle sizes of particles of sorbic acid after passing through ASTM No. 400 mesh sieve were observed by means of a microscope. As a result, the particles consisted of about 10% of particles of 20 μ or larger, about 30% of particles of 10μ–20 μ and about 60% of particles of 10 μ or smaller.

In addition, in the case of such particle sizes, the optimum range of water content was 18–40%.

EXAMPLES 3–6 and Comparative examples 1–2

Fine powder of sorbic acid obtained in the former half of Example 1 was dried up to a water content of 15% and the resulting powder was mixed with each of the separated powders having various ranges of particles sizes, obtained in the above-mentioned Referential example. The resulting mixtures, after adjustment of water content, were granulated by means of an extrusion type granulator to give results shown in Table 1.

Table 1

| Example or Comparative Example | Particle size of usual sorbic acid (mesh) | Proportion of usual sorbic acid (%) | Proportion of fine powder of sorbic acid (%) | Shape stability after drying |
|---|---|---|---|---|
| Comparative ex. 1 | − 60 | 10 | 90 | Bad (no effect of water content adjustment) |
| " 2 | 60 – 70 | 30 | 70 | Somewhat bad (liable to collapse considerably) |
| Example 3 | 70 – 100 | 60 | 40 | Fairly good (somewhat collapse, but such an extent does not raise any problem) |
| Example 4 | 100 – 140 | 60 | 40 | Good |
| " 5 | 140 – 300 | 80 | 20 | " |
| " 6 | 300 – | 85 | 15 | " |

EXAMPLES 7–10 and Comparative examples 3 and 4

Fine powder of sorbic acid obtained in the former half of Example 2 was dried up to a water content of 18%. Using the resulting powder, the same tests as in Examples 3–6 were carried out to give the following results.

Table 2

| Example or Comparative example | Particle size of usual sorbic acid (mesh) | Proportion of usual sorbic acid (%) | Proportion of fine powder of sorbic acid (%) | Shape stability after drying |
|---|---|---|---|---|
| Comparative ex. 3 | − 60 | 10 | 90 | Bad (no effect of water content adjustment) |
| " 4 | 60 – 70 | 30 | 70 | " |
| Example 7 | 70 – 100 | 50 | 50 | Fairly good (liable to collapse somewhat) |
| " 8 | 100 – 140 | 70 | 30 | Fairly good (somewhat collapse, but no problem) |
| " 9 | 140 – 300 | 75 | 25 | Good |
| " 10 | 300 – | 80 | 20 | " |

EXAMPLE 11

Crystalline sorbic acid obtained according to a conventional method was sieved by ASTM No. 70 sieve, and powder left on the sieve was removed. The particle size distribution of powder having passed through this 70 mesh sieve was as follows:

| 70 | mesh pass | 100 | mesh on | 16% |
| 100 | " | 140 | " | 34% |
| 140 | " | 300 | " | 42% |
| 300 | " | | | 8% |

In addition, the section having passed through ASTM No. 300 sieve contained almost no fine powder of 20 μ or smaller.

To 100 parts of the 70 mesh pass product having the above-mentioned particle size distribution were added 50 parts of fine powder of sorbic acid having a water content of 47%, obtained in the same manner as in the former half of Example 1, and 20 parts of water, and these were mixed together. The composition of the resulting mixture was as follows:

The content of fine powder in the total sorbic acid was 21%, and the content of water in the total amount of the mixture was 26%.

When this mixture was granulated by means of an extrusion type granulator, granulation was very smoothly effected. Also, the shape stability after drying was nearly good.

EXAMPLE 12

The same crystalline sorbic acid product as in Example 11 was separated by sieve. Only the section having passed through ASTM No. 100 sieve was adopted. The particle size distribution of this section was as follows:

| 100 | mesh pass | 140 | mesh on | 41% |
|---|---|---|---|---|
| 140 | " | 300 | " | 50% |
| 300 | " | | | 9% |

To 100 parts of this section were added 30 parts of fine powder of sorbic acid having a water content of 25%, obtained in the same manner as in the former half of Example 2 (according to the results of observation by means of a microscope, about 10% of powder of 20 μ or larger, about 40% of powder of 10–20 μ and about 50% of powder of 10 μ or smaller), and 40 parts of water, and these were mixed together. The composition of the resulting mixture was as follows:

The content of fine powder in the total sorbic acid: 18% the content of water in the total amount of the mixture: 28%

When this mixture was granulated by means of an extrusion type granulator, granulation could be carried out although extrusion was somewhat difficult. The resulting granule appeared to be liable to collapse somewhat, but not to such an extent as to become an issue.

As shown in Examples 11 and 12, if powder of sorbic acid having a relatively broad particle size distribution is employed, granulation was possible in the presence of a lower proportion of fine powder than those anticipated from the results of Examples 3–10 in which the mixing proportion of fine powder was observed with powder having a narrow particle size range.

EXAMPLE 13

A powder product of sorbic acid on sale (made by Chisso Corporation, Japan) was separated by sieve to give samples A-I having particle size distributions shown in Table 3.

Table 3

| Sample | Samples of powder of sorbic acid having different particle size distributions | | | | | Remark |
|---|---|---|---|---|---|---|
| | Mesh pass-on −70 | 70 −100 | 100 −140 | 140 −300 | 300 — | |
| A | 14% | 20% | 27% | 24% | 15% | (Usual product) |
| B | — | 23 | 32 | 28 | 17 | 70 mesh pass |
| C | — | — | 42 | 37 | 21 | 100 " |
| D | — | — | — | 62 | 38 | 140 " |
| E | — | — | — | — | 100 | 300 " |
| F | — | — | 53 | 47 | — | 100 - 300 |
| G | — | — | 48 | 42 | 10 | E-F mixture[1] |
| H | — | — | 50 | 45 | 5 | E-F mixture[2] |
| I | — | — | 51 | 46 | 3 | E-F mixture[3] |

Note:
Mixing ratio (E/E+F), E-F mixture[1]: 10%
E-F mixture[2]: 5%, E-F mixture[3]: 3%

To 1 Kg of each of samples A-I in Table 3 was added 10 g of a sucrose fatty acid ester having a HLB of about 11 (Nitto ester S-1170 (trade name) made by Dainippon Seito K.K., Japan), and these were mixed together by means of a blender. Water was added to the resulting mixture so that the mixture may have a water content of 10% (the amount of water required: about 110 g). The resulting wetted mixture was granulated by means of an extruder (ECK Pelleter (trade name) manufactured by Fuji Denki K.K., Japan). The results of the granulation are shown in Table 4.

Table 4

| | Results of granulation tests with each particle size distribution | | | |
|---|---|---|---|---|
| Sample | Number of repetition of granulation | Shape stability | Percentage collapse into powder (%) | Hardness (g) |
| A | 10 | bad | 100 | — |
| B | 10 | fairly good | 60 | 10 or less |
| C | 2 | good | 1 or less | 190 |
| D | 1 | " | 1 or less | 210 |
| E | 1 | " | 1 or less | 210 |
| F | 10 | fairly good | 20 | 10 |
| G | 2 | good | 1 or less | 180 |
| H | 3 | " | 3 | 90 |
| I | 5 | " | 10 | 20 |

The number of repetition of granulation referred to in Table 4 means the number of times in case where a granulated substance obtained by being once granulated by extrusion (including a substance extruded in the form of powder without being granulated) is again granulated by extrusion. In this case, one time means that there was no repetition. Accordingly, the number of (the above-mentioned number of repetition of granulation minus one) is a correct number of repetition of granulation. The word of the repetition used to denote is almost similar to words of the extension of mixing time or the increase of the revolution number of stirrer in case where a blender is operated. Namely, the uniformity of the composition of a wetted mixture of sorbic acid (containing water and a surfactant) is effected by the repetition.

Next, as for the shape stability, the collapsibility and the smoothness of surface, of the extrusion-granulated substance were visually judged to give three grades (good, fairly good and bad). Only the granulated substances of "good" and "fairly good" are practically usable. This also applies to other Tables herein. As for the effect of the water content employed (suitability of unsuitability), the water content is considered in this Example as having no direct influence on the shape stability. Further, the liability of forming powder was quantitatively expressed by the percentage collapse into powder, mentioned below.

The percentage collapse into powder referred herein means the proportion (%) of the substance having passed through ASTM No. 20 sieve when a granulated substance extruded from an extrusion type granulator is dried at 60° C. for 2 hours in a tray type, air circulation dryer, and then shaked for 10 minutes with a vibration number of 10 times/sec. by means of a sieve shaker (Iwaki sieve shaker R-V-2 type (trade name) made by Iwaki K.K., Japan). This also applies to other Tables herein. As for the meaning of the percentage collapse into powder, the collapsibility of a dried product at the time of handling (including a substance extruded in the form of powder without being granulated, at the time of extrusion-granulation) is quantitatively expressed by the percentage collapse into powder.

As for the hardness, a load was applied onto each of individual dried granules of sorbic acid to observe the number of gram at the time of collapse, and the average value of those of 30 granules was taken with each sample. This also applies to other Tables herein.

Based on the conditions of Table 3 and the results of Table 4, particle size distribution and capability of being granulated, of powder of sorbic acid in this Example will be mentioned below.

Sample A containing a large amount of powder of 100 mesh on cannot be granulated.

Sample B containing a considerable amount of powder of 70-100 mesh is high in the percentage collapse into powder and extremely insufficient in the hardness, but, nevertheless, is on the borderline of granulation-possibility.

Sample C containing a large amount of powder of 100-140 mesh gave a good result by twice repetitions, while sample F obtained by removing extremely fine powder of 300 mesh pass from sample C was reduced in the percentage collapse into powder down to a desirable extent, by 10 times repetitions, but its hardness is low as in the case of sample B.

Further, as seen from the granulation results with samples C, D, E and G, the presence of 10% or more of the section of powder of 300 mesh pass gives the best result. However, as apparent from the granulation results with sample F, the presence of the section of powder of 300 mesh pass is not indispensable for reducing the percentage collapse into powder down to a suitable extent. On the other hand, in the case of samples having no section of powder of 300 mesh pass or having less than 10% of the section, it is necessary to sufficiently mix the mixture of powder of sorbic acid, water and a surfactant (in this Example, granulation was repeated many times i.e. from several to 10 times). In conclusion, it is desirable that powder of sorbic acid having particle sizes of 100 mesh pass, to be employed in the method of the present invention contains 10% or more of extremely fine powder having particle sizes of 300 mesh pass, because (i) even a light mixing is sufficient and (ii) the hardness of the resulting granular product is increased.

Comparative example 5

To 1 Kg of powder of sorbic acid having the same particle size distribution as that of sample A of Example 13 was added 20 g of a sucrose fatty acid ester (HLB: about 15, DK ester F 160 (trade name) made by Daiichi Kogyo Seiyaku K.K., Japan) and these were mixed together. While 110 g of water was portion-wise mixed with the mixture obtained above, granulation was repeated as in Example 13. When the number of repetition of granulation exceeded 25 times, the shape stability became better. Further, at the time of 30 times, the percentage collapse into powder became 20%. In this case, it is presumed that at the time of 25 times, the section of powder of 70 mesh or smaller of sample A (14%) might have been substantially pulverized and converted into a section of powder having intermediate particle sizes between those of sample B and sample C of Table 3.

EXAMPLE 14 and Comparative examples 6 and 7

To 1 Kg of powder of sorbic acid having the same particle size distribution as that of sample G of Example 13 were added a sucrose fatty acid ester (HLB: about 15, DK ester F 160 (trade name)) and sorbitan monostearate (HLB: 4.7, Nissan Nonion SP-60 (trade name) made by Nihon Yushi K.K., Japan), each in a proportion shown below in Table 5 and so as to give a total sum amount of 10 g, and these were mixed together. While 350 g or smaller of water was portion-wise mixed with the mixture obtained above, granulation was repeated as in Example 13 to give the following results shown in Table 5 (results of (a) - (f) and results of Comparative examples 6 and 7), in accordance with the mixing proportions of the above-mentioned two kinds of surfactants:

Table 5

Results of granulation tests with different HLBs

| | Surfactant (g) | | | Number of times of granulation | Water content required (%) | Shape stability | Percentage collapse into powder (%) | Hardness (g) |
|---|---|---|---|---|---|---|---|---|
| | F-160 | SP-60 | HLB | | | | | |
| (a) | 10 | 0 | 15 | 1 | 5 | good | 1 | 150 |
| (b) | 6 | 4 | 10.9 | 2 | 9 | " | 1 | 180 |
| (c) | 4 | 6 | 8.8 | 3 | 11 | " | 1 | 200 |
| (d) | 3 | 7 | 7.8 | 4 | 13 | " | 1 | 170 |
| (e) | 2.5 | 7.5 | 7.3 | 5 | 14 | " | 2 | 120 |
| (f) | 2.2 | 7.8 | 7.0 | 5 | 15 | " | 4 | 80 |
| Comparative ex. 6 | 2 | 8 | 6.8 | 10 | 25 | fairly good | 80 | 10 or less |
| Comparative ex. 7 | 0 | 10 | 4.7 | 20 | — | bad | 100 | — |

As apparent from Table 5, in the case of a HLB of 7.0 or more, granule of sorbic acid having a good hardness can be obtained by employing a number of repetition of granulation of 5 times or less and 15% or less of water based on the powder of sorbic acid, whereas, in the case of a HLB of 6.8 or 4.7 (Comparative examples 6 or 7), the shape stability and the percentage collapse into powder were both insufficient.

EXAMPLE 15 and Comparative example 8

With powder of sorbic acid having the same particle sizes as those of sample E of Example 13 was mixed a sucrose fatty acid ester (HLB: about 15, DK Ester F 160 (trade name)) in various proportions (% by weight) shown below in Table 6. Water in various proportions was mixed with each of the mixtures obtained above, followed by granulation by means of an extrusion type granulator as in Example 13. Among the granulated substances obtained from the mixtures containing a surfactant in various proportions, and being in a satisfactory state, those of the least amount of water added were subjected to a measurement of water content according to Karl Fischer's method. Further the qualities of granules obtained by drying the granulated substances were observed. The results are shown in Table 6. The granulation was always once carried out.

Table 6

Results of granulation tests with various amounts of surfactant

| Symbol | Amount of surfactant (%) | Least water content required (%) | Shape stability | Water content after drying (%) | Percentage collapse into powder (%) | Hardness (g) |
|---|---|---|---|---|---|---|
| (a) | 4 | 4 | good | 0.4 | 1 or less | 200 |
| (b) | 2 | 4 | " | 0.3 | 1 or less | 210 |
| (c) | 1 | 4 | " | 0.1 | 1 or less | 200 |
| (d) | 0.5 | 4 | " | 0.2 | 1 or less | 190 |
| (e) | 0.1 | 10 | " | 0.2 | 1 or less | 140 |
| (f) | 0.05 | 14 | " | 0.2 | 2 | 100 |
| (g) | 0.02 | 20 | " | 0.2 | 5 | 50 |
| Comparative ex. 8 | 0 | 25 | fairly good | 0.2 | 40 | less than 10 |

As apparent from Table 6, in case where 0.02% or more of a surfactant is mixed, the percentage collapse into powder is very low and also the hardness is sufficient, whereas, in case where no surfactant is used (Comparative example 8), the percentage collapse into powder is high and also the hardness is insufficient. This shows that even if extremely fine powder as small as 300 mesh pass occupies the total amount of powder employed, it is impossible to attain the objects of the above-mentioned methods (5) - (7) of the present invention, unless a surfactant (having a HLB of 7 or more) is employed.

Comparative example 9

In this Comparative example, the same powder of sorbic acid as those of Example 13 was employed. As the surfactant, sorbitan monopalmitate (HLB: 6.7, Span 40 (trade name) made by Kao Atlas Kogyo K.K., Japan), sorbitan monolaurate (HLB: 8.6, Nissan Nonion LP-20 (trade name) made by Nihon Yushi K.K., Japan), a sucrose fatty acid ester (HLB: about 15, DK Ester F 160 (trade name)), an edible oil glyceride (HLB: 3.5, Atmul 124 (trade name) made by Atlas Chemical Industries Co., U.S.A.) and a lactic acid ester of edible oil glyceride (HLB: 2.6, Atmul 200 (trade name) made by said company) were employed. Each of these surfactants was mixed with 1 Kg of powder of sorbic acid in mixing proportions shown below in (a)-(c) of Table 7. While 250 g or less of water was portion-wise mixed with the mixtures obtained above, extrusion-granulation was repeated. As a result, in any of the cases, the shape stability at the time of granulation was almost good, but the percentage collapse into powder after drying was about 30% in the best case, even when the mixing proportion of water was varied to any one, and it was impossible to reduce the above-mentioned value to less.

Table 7

Granulation tests with various kinds of surfactants

| Symbol | Surfactant | Amount added (g) | HLB (average) | Percentage collapse into powder (Number of repetition of granulation) |
|---|---|---|---|---|
| a. | Span 40 | 50 | 6.7 | 40 |
| b. | LP-20 | 32 | | |
| | Atmul 124 | 18 | 6.8 | 30 |
| c. | DK Ester F 160 | 16 | | |
| | Atmul 200 | 34 | 6.6 | 40 |

When these results are compared with those of the above-mentioned Example 15 and Comparative example 8, it is apparent that even when any of the surfactants or mixtures thereof (a)-(c) of Table 7 are employed, if the value of HLB is less than 7, no desirable result can be obtained whatever the water content and the mixing manner (number of repetition of granulation) may be.

EXAMPLE 16

The same powder of sorbic acid on sale as those employed in Example 13 was separated by ASTM No. 100 sieve. To 2 Kg of the resulting powder of 100 mesh on was added 2 g of a sucrose fatty acid ester (HLB: 13, DK Ester F 140 (trade name) made by Daiichi Kogyo Seiyaku, Japan), and the mixture was pulverized by means of a pulverizer to give a pulverized raw material having the following particle size distribution.

Particle size distribution of pulverized material

| Section of particle sizes (mesh) | Proportion (%) | Note |
|---|---|---|
| - 70 | 0 | 70 mesh on |
| 70 - 100 | 2 | |
| 100 - 140 | 19 | |
| 140 - 300 | 54 | |
| 300 - | 25 | 300 mesh pass |

One Kg of the raw material was mixed with 150 g of water and the resulting mixture was granulated by means of an extrusion type granulator.

A granulated substance having a good shape stability was obtained by three times repetition of granulation. The percentage collapse into powder and the hardness, of the granular product obtained by aeration-drying the granulated substance were 1% and 120 g, respectively.

As apparent from the above-mentioned results, the powder of sorbic acid (crystalline) to be employed for preparing the granule of the present invention is not necessarily those which have been originally precipitated as crystals, but may be those which are obtained by mechanical pulverization and whose particle sizes fall within a section having given particle sizes. Further, even when a small amount of a section of 100 mesh on (2% of a section of 70-100 mesh) is contained, the granular product aimed in the method of the present invention can be obtained.

Comparative example 10

2 Kg of powder of sorbic acid on sale having a particle size distribution (a) mentioned below (made by Taisho K.K., Japan) was added 40 g of the same sucrose fatty acid ester as that employed in Example 16, followed by pulverization in the same manner as in Example 16 to give a pulverized mixture having the following particle size distribution (a').

| (a) Particle size distribution before pulverization | | |
|---|---|---|
| Section of particle sizes (mesh) | Proportion (%) | Note |
| − 70 | 71 | 70 mesh on |
| 70 − 100 | 19 | |
| 100 − 140 | 5 | |
| 140 − 300 | 4 | |
| 300 − | 1 | 300 mesh pass |

| (a'n) Particle size distribution after pulverization | | |
|---|---|---|
| Section of particle sizes (mesh) | Proportion (%) | Note |
| − 70 | 2 | 70 mesh on |
| 70 − 100 | 11 | |
| 100 − 140 | 42 | |
| 140 − 300 | 30 | |
| 300 − | 15 | 300 mesh pass |

(a) While 100 g of water was successively portionwise mixed with 1 Kg of the above-mentioned unpulverized substance, granulation was carried out by means of an extrusion type granulator to give an undried granular substance having a good shape stability after 5 times granulation, but the percentage collapse into powder, of this substance as measured after aeration-drying was 30%. The principal reason why the results are inferior to those of Example 16 is believed to be due to the fact that the proportion of the section of 70-100 mesh is large.

(a') While 70 g of water was successively portionwise mixed with 1 Kg of the above-mentioned pulverized substance, pulverization was repeatedly carried out by means of a pulverizer, and the resulting flake-like pulverized substance was granulated by extrusion. The pulverized substance was very good in granulation capability, i.e. a granular substance having a stabilized shape was obtained by one granulation step. The percentage collapse into powder and the hardness, of a granular product obtained by aeration-drying the undried granular substance, were 1% and 140 g, respectively.

In order to observe the particle size distribution of powder of sorbic acid of the granular product obtained above, 500 g of water was added to 100 g of the granule, and these were vigorously stirred by means of a homogenizer while being heated at 50° C., to collapse the granule completely. The resulting dispersed suspension was allowed to stand for 2 hours to separate the resulting precipitate. The separated precipitate was subjected to three repetitions of operations of water-washing, being allowed to stand and decantation, followed by drying in vacuo and separating the resulting dried powder by ASTM No. 100 sieve to give 3 g of a section of 100 mesh on. In addition, the water layer separated by decantation was filtered by ASTM No. 100 sieve, but no powder of sorbic acid was left behind on the sieve.

The reason that the granulation results of the above-mentioned (a') are superior is believed to be due to the fact that the particle size distribution of powder of sorbic acid as raw material is superior to that of the above-mentioned (a), i.e. the amount of the section of 100 mesh on is smaller.

EXAMPLE 17

37 Kg of raw powder of sorbic acid was dissolved in 1000 l of hot water (at 98° C.), and the resulting solution was mixed with 1 Kg of powdery activated carbon to subject the solution to decolorization treatment. The activated carbon was separated by filtration from the solution and the filtrate was rapidly cooled, followed by decantation to remove by separation the most part of water. To the resulting slurry of sorbic acid were added 100 g of a sucrose fatty acid ester (HLB: 13, DK Ester 140 (trade name)) and 70 g of propyleneglycol monostearate (HLB: 3.4, Homotex PS 90 (trade name)) made by Kao Atlas K.K., Japan), and they were mixed together and dispersed. The proportion of the total sum of the amounts of the two kinds of surfactants used, based upon the weight of the original raw powder of sorbic acid, was 0.46%, and the average value of the HLBs of surfactants was about 9. The resulting suspension of sorbic acid was separated by filtration by means of centrifuge to give about 36 Kg of a cake of sorbic acid having a water content of 11%.

Particle size distribution of decolorized powder of sorbic acid

| Section of particle size (mesh) | Proportion (%) | Note |
|---|---|---|
| − 70 | 0 | 70 mesh on |
| 70 − 100 | trace | |
| 100 − 140 | 11 | |
| 140 − 300 | 31 | |
| 300 − | 58 | 300 mesh pass |

To the cake of sorbic acid was added sodium tripolyphosphate in the proportions described below in Table 8, and these were mixed together, followed by extrusion-granulation and drying to give the results shown in the following Table 8.

Table 8

Results of granulation tests with different amounts of sodium tripolyphosphate used

| Sample No. | Proportion of amount of Na tri-polyphosphate added (%)* | Number of repetition of granulaton | Shape stability | Water content after drying (%) | Percentage collapse into powder (%) | Hardness (g) | Collapsibility (min) |
|---|---|---|---|---|---|---|---|
| a | 0 | 1 | good | 0.2 | 1 or less | 130 | 30 |
| b | 0 | 3 | " | 0.2 | 1 " | 200 | 30 |
| c | 0 | 5 | " | 0.2 | 1 " | 220 | 30 |

Table 8-continued

| | Results of granulation tests with different amounts of sodium tripolyphosphate used | | | | | | |
|---|---|---|---|---|---|---|---|
| Sample No. | Proportion of amount of Na tripolyphosphate added (%)* | Number of repetition of granulaton | Shape stability | Water content after drying (%) | Percentage collapse into powder (%) | Hardness (g) | Collapsibility (min) |
| d | 0.05 | 3 | " | 0.2 | 1 " | 150 | 1 |
| e | 0.5 | 3 | " | 0.2 | 2 | 80 | 0.5 or less |
| f | 1 | 3 | " | 0.3 | 4 | 50 | 0.5 " |

Note:
Symbol* shows % based on the weight of powder of sorbic acid.

As apparent from Table 8, the additive effectiveness of the small amount of sodium tripolyphosphate consists mainly in the improvement of collapsibility. On the other hand, the hardness is reduced, but such a hardness as 50 g corresponds to a practically sufficient strength. With regard to the objective foods to which a small amount of sodium tripolyphosphate is apparently to be added in a separate process, the use of a granular sorbic acid containing a small amount of sodium tripolyphosphate as in this Example ((d), (e) and (f)) is not considered to be disadvantageous as compared with the use of a granular sorbic acid which does not contain it.

Comparative example 11

A sufficient amount of crystalline sorbic acid was dissolved in 10 l of hot water at 98° C. to make a hot saturated aqueous solution. This solution, while being maintained at 98°-99° C., was spouted into a vessel maintained under a reduced pressure of 30-40 mmg, whereby extremely fine powder of sorbic acid was precipitated by the reduction in temperature at the time of spouting to give a suspension of sorbic acid. Thereafter the suspended particles in the suspension were separated by sedimentation, followed by filtration under a reduced pressure to give 590 g of powder of sorbic acid having a water content of 51% (a cake). A part of this cake was sampled and a surfactant was added thereto, and the mixture was dispersed in water, followed by observing the particle sizes of the resulting dispersion by means of a microscope. As a result, almost all particles had particle sizes of 1µ or smaller. 410 Gram of this cake of sorbic acid consisting of extremely fine powder and having a water content of 51% was added to 600 g of raw material E of Example 13, and they were uniformly mixed together, followed by extrusion-granulation by means of an extrusion type granulator to give a granulated substance (water content: about 21%) having a stabilized shape, by one granulation step. The percentage collapse into powder and the hardness, of granules obtained by drying the granulated substance were 8% and 30 g, respectively.

Further, when these granules were introduced into warm water at 40° C., no collapse occurred unless stirring was carried out, i.e. collapsibility was inferior.

As apparent from the above-mentioned fact, granules of sorbic acid having no surfactant added and having a considerable amount of extremely fine powder of sorbic acid admixed, are good in the granulation capability of powder, but relatively small in the hardness and insufficient in the collapsibility in water as compared with those obtained according to the above-mentioned methods (5)-(7).

EXAMPLE 18

With powder of sorbic acid having the same particle size distribution as that of sample E of Example 13 was mixed a polyoxyethylene sorbitan monostearate (HLB: about 14.9, Tween 60 (trade name) made by Atlas Chemical Industries, U.S.A.) in various proportions (% by weight) shown below in Table 9. Water was mixed with each of the mixtures obtained above, in various proportions, followed by extrusion-granulation by means of an extrusion type granulator as in Example 13. Among the granulated substances obtained from powders having a surfactant added in various proportions, and being in a satisfactory state, those of the least amount of water added were subjected to a measurement of water content according to Karl Fischer's method, and also the qualities of granule obtained by drying the granulated substance were observed, to give the results shown in Table 9. Any of the granulations were carried out by one time step.

Table 9

| | Results of granulation tests with different amounts of polyoxyethylene sorbitan monostearate used | | | | | |
|---|---|---|---|---|---|---|
| Symbol | Surfactant (%) | Least amount of water required (%) | Shape stability | Water content after drying (%) | Percentage collapse into powder (%) | Hardness (g) |
| a | 2 | 2 | good | 0.5 | 1 or less | 350 |
| b | 1 | 2 | " | 0.3 | 1 or less | 320 |
| c | 0.5 | 3 | " | 0.2 | 1 or less | 270 |
| d | 0.1 | 5 | " | 0.2 | 1 or less | 210 |
| e | 0.05 | 8 | " | 0.2 | 1 or less | 160 |
| Comparative ex. 8 | 0 | 25 | fairly good | 0.2 | 40 | less than 10 |

As apparent from Table 9, if 0.05% or more of the surfactant is mixed, the percentage collapse into powder is very low and also the hardness is sufficient, whereas, if the surfactant is not used (Comparative example 8, again listed), the percentage collapse into powder is high and also the hardness is insufficient. This shows that even if extremely fine powder as small as 300 mesh pass occupies the total amount of powder, if no surfactant (having a HLB of 7 or more) is employed, it is impossible to attain the objects of the present invention.

EXAMPLE 19

To 1 Kg of powder of sorbic acid having the same particle size distribution as that of sample B of Example 13 were added 10 g of each of mixtures of surfactants having different HLBs of 4.6–6.9, obtained by mixing a polyoxyethylene sorbitan monostearate (the same product as that employed in Example 18) with an edible oil glyceride (HLB: 3.5, Atmul 124 (trade name) made by Atlas Chemical Industries, U.S.A.), and they were mixed together. While 250 g of water was portion-wise mixed with the mixtures obtained above, extrusion-granulation was repeated 5 times, to give results which were all practically usable, as shown below in Table 10, although the amounts of water required were different.

Table 10
Results of granulation tests with mixtures of polyoxyethylene sorbitane monostearate having HLBS less than 7

| Symbol | HLB | Amount of water used (%) | Shape stability | Water content after drying (%) | Percentage collapse into powder (%) | Hardness (g) |
|---|---|---|---|---|---|---|
| a | 6.9 | 12 | good | 0.3 | 2 or less | 120 |
| b | 5.8 | 18 | " | 0.2 | 5 or less | 70 |
| c | 4.6 | 25 | " | 0.2 | 10 or less | 50 |

As apparent from Table 10, when as a polyoxyethylene sorbitan ester, its monostearate is mixed and used, it is possible to prepare a practically usable granule, even if the HLB is less than 7.

EXAMPLE 20

Granulation tests were carried out using as raw material sorbic acid, the same sorbic acid on sale (not yet pulverized) as that employed in Comparative example 10, and as surfactant, each of three kinds of surfactants (single use) of a polyoxyethylene sorbitan monolaurate (HLB: 16.7, Tween 20 (trade name) made by Atlas Chemical Industries, U.S.A.), a polyoxyethylene sorbitan monostearate (HLB: 14.9, Nissan Nonion ST-221 (trade name) made by Nihon Yushi K.K., Japan) and a polyoxyethylene sorbitan monooleate (HLB: 15.0, Tween 80 (trade name) made by Atlas Chemical Industries).

Namely, 10 g of each of said surfactants was dissolved or dispersed in 50 g of water. The resulting liquid was mixed with 1 Kg of said sorbic acid. Further while 80–100 g of water was portion-wise mixed, extrusion-granulation was repeated 15 times. The resulting granulated substances were dried at 60° C., for 4 hours by means of a tray and compartment, air circulation type dryer. The results are shown in Table 11.

Table 11
Results of granulation tests with various polyoxyethylene sorbitan fatty acid esters having a HLB of 7 or more

| Symbol | Surfactant | HLB | Shape stability | Water content after drying (%) | Percentage collapse into powder (%) | Hardness |
|---|---|---|---|---|---|---|
| a | Tween 20 | 16.7 | good | 0.2 | 2 | 140 |
| b | ST-221 | 14.9 | " | 0.1 | 4 | 110 |
| c | Tween 80 | 15.0 | " | 0.2 | 4 | 100 |

As apparent from the results of Examples 19 and 20, when polyoxyethylene sorbitan fatty acid esters are employed, granule which is satisfactory for practical use can be obtained, even if raw material powder of sorbic acid contains a large amount of powder having particle sizes of 100 mesh on.

However, if the objects of the present invention such as (i) problems relative to hygiene of operation environment such as prevention of scattering of powder, etc. (ii) uniformity of dispersion of granules into foods, obtained according to the method of the present invention, etc. are taken into consideration, granulation of large powder of sorbic acid such as those in which powder of 70 mesh on occupies the most part, is of no meaning in practical viewpoint.

Of course, even when such large powder is empolyed as raw material, granule having an improved uniformity in dispersion into foods can be prepared if a kneader having a pulverization performance at the same time is used, but this has the same meaning as granulation carried out using a raw material which has been pulverized in advance.

What is claimed is:

1. A method for producing a granular sorbic acid which consists of granulating by extrusion a powder of sorbic acid having particle sizes of ASTM No. 70 sieve pass in the presence of a material selected from the group consisting of (a) water and (b) water containing a surfactant.

2. A method according to claim 1 wherein said powder of sorbic acid having particle sizes of ASTM No. 70 sieve pass consists of a mixture of less than 80% by weight of said powder with 20% by weight or more of a fine powder of sorbic acid having particle sizes of 20μ or smaller and said granulation is carried out in the presence of water.

3. A method according to claim 1 wherein said powder of sorbic acid having particle sizes of ASTM No. 70 sieve pass consists of (1) 50–75% by weight of a powder of sorbic acid having particle sizes within the range of ASTM No. 70 sieve pass to ASTM No. 300 sieve on and (2) 50–25% by weight of fine powder of sorbic acid having particle sizes of 20μ or smaller.

4. A method according to claim 1 wherein said powder of sorbic acid having particle sizes of ASTM No. 70 sieve pass consists of (1) 50–75% by weight of a powder of sorbic acid having particle sizes within the range of ASTM No. 70 sieve pass to ASTM No. 300 sieve on and (2) 50–25% by weight of a fine powder of sorbic acid having particle sizes of 20μ or smaller, and said granulation is carried out in the presence of water.

5. A method according to claim 3 wherein the amount of water used is in the range of 10–50% by weight based on the total weight of sorbic acid and water.

6. A method according to claim 4 wherein the amount of water used is in the range of 10–50% by weight based on the total weight of sorbic acid and water.

7. A method for producing a granular sorbic acid which consists of granulating by extrusion a powder of sorbic acid having particle sizes of ASTM No. 100 sieve pass in the presence of water and a surfactant having a HLB of at least 7.

8. A method according to claim 1 wherein a powder of sorbic acid having particle sizes of ASTM No. 70 sieve pass is granulated by extrusion in the presence of water and a surfactant having a HLB of less than 7 and containing a polyoxyethylene sorbitan fatty acid ester.

9. A method according to claim 7 wherein the amounts of water and said surfactant used are in the ranges of 4–15% by weight and 0.02–1.0% by weight respectively, based on the weight of said powder of sorbic acid.

10. A method according to claim 8 wherein the amounts of water and said surfactant used are in the ranges of 4–15% by weight and 0.02–1.0% by weight respectively based on the total weight of water and said powder of sorbic acid.

11. A method according to claim 1 wherein the resulting product obtained by said granulation by extrusion is granulated by extrusion at least once again.

* * * * *